United States Patent [19]

Palermo

[11] Patent Number: 5,312,415
[45] Date of Patent: May 17, 1994

[54] ASSEMBLY FOR PLACEMENT OF EMBOLIC COILS USING FRICTIONAL PLACEMENT

[75] Inventor: Thomas J. Palermo, San Jose, Calif.

[73] Assignee: Target Therapeutics, Inc., Fremont, Calif.

[21] Appl. No.: 949,095

[22] Filed: Sep. 22, 1992

[51] Int. Cl.⁵ .................... A61B 17/00; A61M 29/00
[52] U.S. Cl. ................................ 606/108; 606/191
[58] Field of Search ............ 606/194, 191, 200, 159, 606/108, 151, 198; 604/159, 164; 128/772

[56] References Cited

U.S. PATENT DOCUMENTS

| | | |
|---|---|---|
| 3,334,629 | 8/1967 | Cohn . |
| 4,739,768 | 4/1988 | Engelson . |
| 4,813,934 | 3/1989 | Engelson . |
| 4,830,003 | 5/1989 | Wolff et al. .................... 606/191 |
| 4,884,579 | 12/1989 | Englelson . |
| 4,957,501 | 9/1990 | Lahille et al. . |
| 4,994,069 | 2/1991 | Richart et al. . |
| 5,037,427 | 8/1991 | Harada et al. .................... 606/194 |
| 5,108,407 | 4/1992 | Geremia et al. . |
| 5,109,867 | 5/1992 | Twyford, Jr. . |
| 5,122,136 | 6/1992 | Gugliemi . |

FOREIGN PATENT DOCUMENTS 91-17789 11/1991 PCT Int'l Appl. ................ 606/198

*Primary Examiner*—Tamara L. Graysay
*Attorney, Agent, or Firm*—Morrison & Foerster

[57] ABSTRACT

This invention is a surgical instrument and specifically is a device for delivering embolic coils to a selected site within the vasculature of the human body via use of a catheter. Specifically, a pusher sheath within the catheter lumen pushes embolic coils mounted on a guidewire through the end of the catheter lumen. The catheter may have a constricted distal tip or other means of controlling the release of the embolic coils. Additionally (or alternatively), the guidewire may engage the embolic coils from their interior to allow precise placement of the coils.

7 Claims, 1 Drawing Sheet

ASSEMBLY FOR PLACEMENT OF EMBOLIC COILS USING FRICTIONAL PLACEMENT

FIELD OF THE INVENTION

This invention is a surgical instrument and specifically is a device for delivering embolic coils to a selected site within the vasculature of the human body via use of a catheter. Specifically, a pusher sheath within the catheter lumen pushes embolic coils mounted on a guidewire through the end of the catheter lumen. The catheter has a constricted distal tip or other means of frictionally controlling the release of embolic coils. Additionally (or alternatively), the guidewire may engage the embolic coils from their interior to allow precise placement of the coils.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatment are shown in U.S. patent application Nos. 07/806,898, now U.S. Pat. No. 5,234,437 ("Detachable Pusher-Vasoocclusive Coil Assembly with Threaded Coupling") and 07/806,912, pending ("Detachable Pusher-Vasoocclusive Coil Assembly with Interlocking Ball and Keyway Coupling"). These show methods and devices for delivery of coils or wires within the human body to sites such as aneurysms, to occlude those sites. Coils such as are discussed in those two documents (as well as in U.S. Pat. No. 4,994,069), may be of a regular or helical configuration or assume a random convoluted configuration at the site. The coils normally are made of a radiopaque, biocompatible metal such as platinum, gold, tungsten, or alloys of these and other metals. In treating aneurysms it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray techniques and allows a catheter to be navigated through extremely tortuous vessels, even those surrounded by soft tissue such as the brain.

Once the site has been reached, the catheter lumen is cleared by removing the guidewire (if a guidewire has been used), and one or more coils are placed into the proximal open end of the catheter and advanced through the catheter with a pusher. Pushers are wires having distal ends adapted to engage and push the coil through the catheter lumen as a pusher itself is advanced through the catheter. Once the coil reaches the distal end of the catheter, it is discharged from the catheter by the pusher into the vascular site. This technique of discharging the coil from the distal end of the catheter has a number of undesirable limitations. First, because of the plunging action of the pusher and the coil, the positioning of the coil at the site cannot be controlled to a fine degree of accuracy. Second, once the coil has left the catheter, it is difficult to reposition or retrieve the coil if such is desired.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil is shown in U.S. patent application 07/806,912, pending. In that document, a coil having an enlarged portion is mated with a pusher having a keyway adapted to receive the enlarged portion of the coil in an interlocking relationship. The joint between the pusher and the coil is covered by a coaxial member. The coaxial member is movable by sliding the member axially. As the coaxial member is moved away from the junction where the coil's member engages the keyway of the pusher, the coil is freed from the catheter assembly and the pusher may then be removed.

Another device for placement of coils is shown in U.S. patent application 07/806,898, now U.S. Pat. No. 5,234,437 includes a coil having a helical portion at least one end and a pusher wire having a distal end that is threaded inside of the helical coil by use of a threaded section or the outside of the pusher. The device operates by engaging the proximal end of the coil with a sleeve and unthreading the pusher from the coil. Once the pusher is free, the sleeve may be used to push the coil out into the targeted treatment area.

Another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection having a heat sensitive adhesive. Laser energy is transferred through a fiber optic cable which terminates at that connector. The connector becomes warm and releases the adhesive bond between the connector and the coil.

U.S. Pat. No. 3,334,629, to Cohn, suggests the use of a pusher having a socket to push an occlusive device into the inferior vena cava. However, the rounded end is not used to retain the occlusive device within the end of the inserter.

None of the disclosed devices suggest the use of a catheter having a constricted or feathered end to retain embolic coils on a guidewire for precise placement using a pusher sheath. None of the disclosed devices is capable of delivering a number of coils loaded on one pusher thereby eliminating the need to remove the guide wire from the catheter and re-insert it between coil deliveries.

SUMMARY OF THE INVENTION

One aspect of this invention is a detachable pusher-coil assembly for use in occluding a selected site within a human's vasculature comprising:

(a) a catheter sheath preferably having a constricted tip at its distal end;

(b) a guidewire, optionally with a steerable tip at its distant or distal end, located within the catheter sheath, which guidewire is optionally capable of internally engaging the embolic coils;

(c) at least one embolic coil on the guidewire proximal of the distal end of the guidewire;

(d) a pusher sheath fitting coaxially within the catheter sheath, the guidewire passing through it, and located proximally of the coils on that guidewire.

The pusher sheath will push one or more embolic coils out through the end of the catheter sheath, which end is preferably constricted or otherwise capable of frictionally controlling the movement of those coils through the distal end of the catheter sheath. The pusher sheath also moves the embolic coils over the tip of the guidewire. When used, the constricted tip of the catheter controls the number of coils exiting the catheter with relative ease depending upon the axial movement of the pusher sheath. As an alternative, the interior of the embolic coils may be sized so that a helical wire on the guidewire tip engages the inside of the embolic coils in a nut-and-bolt relationship so that the steerable tip may be screwed through the interior of the most distal embolic coil before it is released. Alternatively, an auger may be placed on the proximal end of the steerable tip to wind its way through the interior of the embolic coils if the size differential between the steerable tip and the embolic coil is sufficiently large.

Another portion of this invention is a method for occluding a selected site within a vessel comprising the steps of:

(a) accessing the site with the distal end of a catheter;

(b) advancing the above-described assembly through the catheter with one or more embolic coils located within the catheter sheath but at a position at the distal end of the catheter sheath;

(c) pushing one or more embolic coil out from the constricted end of the catheter sheath using the pusher sheath and withdrawing the guidewire with its tip through the then most-distal embolic coil; and (d) withdrawing the catheter assembly from the vessel.

Figure 1:
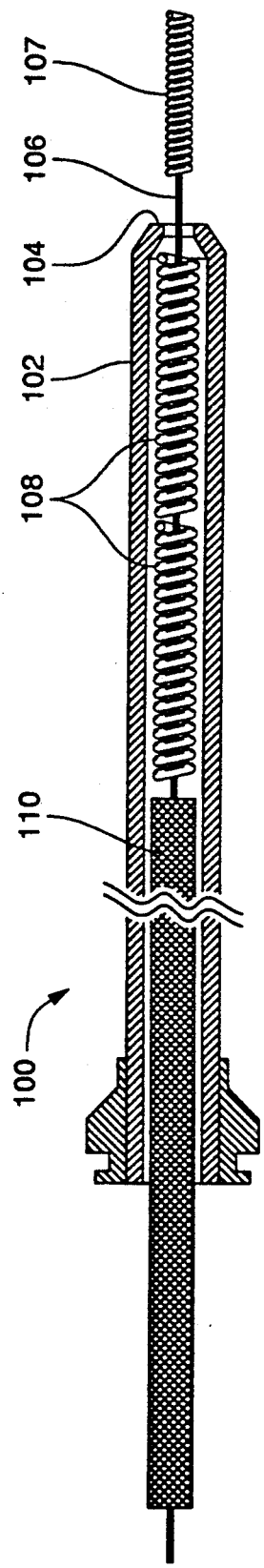
FIGS. 1-3 are enlarged semi-cross-sectional views of the pusher embolic coil assembly of the invention showing the release of the coil from the distal end of the catheter.

In the drawings, it is my convention that proximal is to the left of the drawing and distal is to the right of the drawing.

DESCRIPTION OF THE INVENTION

The assembly, generally designated (100), is shown in FIG. I, and is made up of four principal parts:

(a) a catheter sheath (102) having a distal end (104) which is shown to be constricted but may be of other frictionally engaging shapes suitable for controlling the discharge of the coil through the catheter sheath distal tip;

(b) a guidewire (106) having a tip (107), which desirably is steerable;

(c) one or more coils (108) for placement at the treatment target site; and (d) a pusher sheath (110) located coaxially and somewhat loosely within catheter sheath (102).

Coils (108) are shown in FIG. 1 as uniform diameter helical coils in a straight configuration. Obviously, the coils (108) may be of the type which, upon release from the catheter, either maintain the straight configuration or acquire some other form, e.g., a random configuration or as shown in U.S. Pat. No. 4.994,069. The coils (108) must be dimensioned so as to fit through the inner diameter of catheter sheath (102) as well as fit over the guidewire (106). Typically, the pusher sheath (102) is the sole motivator of the coils although, as noted below, a tip attached to the guidewire may assist in the placement of the coils. In any case, the movement of the coil from the distal end of the catheter must be accomplished with relative ease.

The coils (108) themselves desirably are made of a radiopaque, physiologically compatible material. This material may be platinum, gold, tungsten, or alloys of these metals. This selection of materials is typically done so that the procedure of locating the coils within the vasculature may be made using radiography. However, it also contemplated that the coils may be of various biologically inert polymers or of carbon fiber. A conjunct suitable metallic marker may be appropriate in those instances where the coil material is not sufficiently radio opaque.

The size of the coil and its constituent windings will depend upon the use to which the coil will be placed. For occluding peripheral or neural sites, the coils will typically be made of 0.05 to 0.15 mm diameter wire as wound to have an inner diameter of 0.15 to 1.5 mm with a minimum pitch—that is to say that the pitch is equal to the diameter of the wire used in the coil. The length of the coil will normally be in the range of 0.1 to 60 cm, preferably 0.2 to 40 cm. For other treatments, coils of larger diameter and length may be desired.

If desired, the coil may be formed so that it is essentially linear as it passes through the catheter and yet assume a randomly oriented relaxed condition after it is released from the distal end of the catheter. A discussion of this variation may be found in U.S. Pat. No. 4,994,069.

Coils (108) are slipped onto guidewire (106). Guidewire (106) may have at its distal end a steerable segment (107). Steerable tip (107) is typically made up of a fine winding of wire wrapped about the distal portion of guidewire (106). The tip need not be of the steerable type, e.g., it may instead be of a short length of a coil winding or a mere deposit of a polymer or a metal, but of a size able to just engage the interior of the coil (108) in a frictional manner and allow meticulous control of the coil discharge by the pusher sheath (110). The pusher sheath (110) is placed proximally on the guidewire (106) within the catheter sheath (102). This system allows several coils (108) to be loaded on the proximal end of a guidewire before or during a procedure. The pusher sheath (110) can advance the coils towards the catheter tip while the guidewire remains within the catheter lumen. The guidewire may be reloaded with additional coils by removing the pusher sheath and the guidewire from the catheter lumen, placing additional coils placed on the guidewire, and re-advancing the guidewire-coil-sheath subassembly into the catheter lumen.

The length of assembly (100) will be such that it is capable of being advanced entirely through the catheter to place one or more coils (108) at the target vascular site and yet having a sufficient portion of the proximal end of the assembly (100) protruding from the proximal end of the catheter so to allow manipulation of the pusher sheath (110). For use in peripheral or neural surgeries, the pusher will normally be about 100-200 cm in length, more normally 130-180 cm in length. The diameter of the pusher sheath e(110) is usually in the range of 0.25 to about 1.50 mm, preferably 0.25 to 1 mm.

Figure 2:
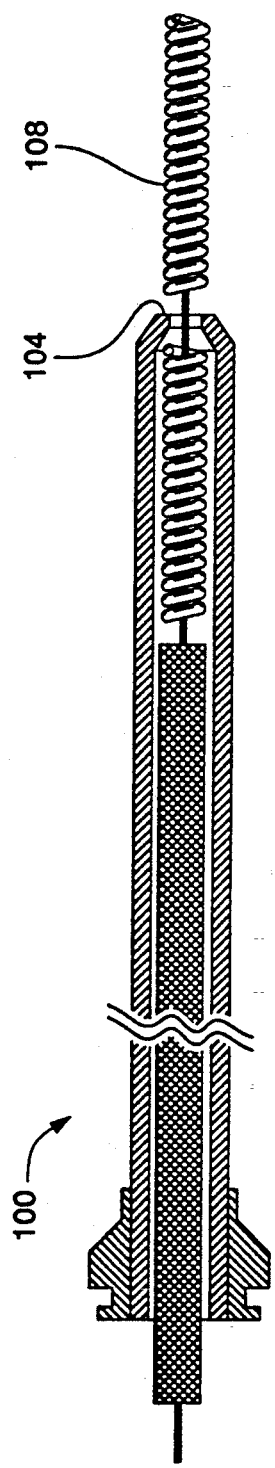

FIG. 2 shows the assembly (100) after the distal end has reached the target site. The guidewire (106) may be retracted or, at the option of the operating physician, be allowed to remain out of the distal section of the assembly (100), and the pusher sheath is advanced to push one coil (108) through the constricted tip (104). The constricted tip (104) prevents additional coils from easily leaving through the catheter tip (104).

Figure 3:
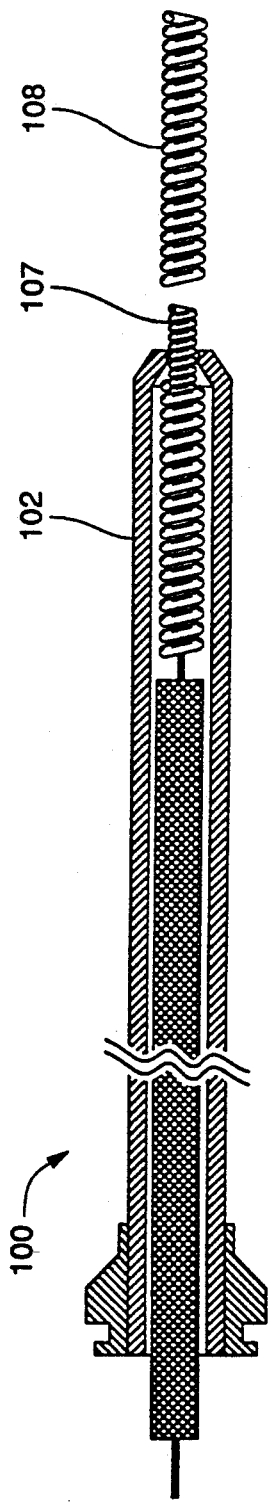

FIG. 3 shows retraction of the guidewire (106) and a steerable tip (107) into the confines of the catheter sheath (102). Embolic coil (108) is free of the assembly (100).

Modifications of the device described above and methods of using it in keeping with this invention that are apparent to having skill in this mechanical and surgical instrument design art and related fields are intended to be within the scope of the claims which follow.

I claim as my invention:

1. A detachable pusher-coil assembly for use in occulding a selected site within a vessel comprising;
   (a) a catheter sheath having a proximal end and a distal end, the distal end having a constricted distal tip, the constricted distal tip having an interior shape to frictionally engage but allow controlled passage of one or more separate embolic coils;
   (b) a guidewire extending from the proximal end to the distal end of the catheter sheath and within the catheter sheath, said guidewire having a tip, said guidewire tip having an outer diameter which approximates an inner diameter of said one or more separate embolic coils, said guidewire tip for frictionally engaging an interior of said one or more embolic coils;
   (c) a plurality of said separate embolic coils situated on said guidewire, each said separate embolic coil having an outer diameter sufficiently large to frictionally engage the constricted distal tip of the catheter sheath;
   (d) a pusher sheath situated within the inside diameter of the catheter sheath proximal to the plurality of separate embolic coils and in which the guidewire passes therethrough, the pusher sheath having a diameter sufficient to be moved axially toward the distal end of the catheter sheath and thereby push said separate embolic coils through the distal end of the catheter sheath.

2. The assembly of claim 1, where each embolic coil includes helical coils.

3. The assembly of claim 2, where each embolic coil is of a straight configuration.

4. The assembly of claim 1 in which the guidewire tip is steerable.

5. The assembly of claim 1 in which each embolic coil is of a radio opaque material.

6. The assembly of claim 5 in which the radio opaque material is selected from platinum, tungsten, gold and their alloys.

7. A method for occluding a selected site within a vessel comprising the steps of:
   (a) providing a pusher-coil assembly including
      (i) a catheter sheath having a proximal end and a distal end, the distal end having a constricted distal tip, the constricted distal tip having an interior shape to frictionally engage but allow controlled passage of one or more separate embolic coils.
      (ii) a guidewire extending from the proximal end to the distal end of the catheter sheath and within the catheter sheath, said guidewire having a tip, said guidewire tip having an outer diameter which approximates an inner diameter of said one or more separate embolic coils, said guidewire tip for frictionally engaging an interior of said one or more embolic coils;
      (iii) a plurality of said separate embolic coils situated on said guidewire, each said separate embolic coil having an outer diameter sufficiently large to frictionally engage the constricted distal tip of the catheter sheath;
      (iv) a pusher sheath situated within the inside diameter of the catheter sheath proximal to the plurality of separate embolic coils and in which the guidewire passes therethrough, the pusher sheath having a diameter sufficient to be moved axially toward the distal end of the catheter sheath and thereby push said separate embolic coils through the distal end of the catheter sheath;
   (b) accessing the site with a distal end of the pusher-coil assembly;
   (c) controlling passage of at least one of the separate embolic coils by:
      (i) advancing the pusher sheath axially toward the distal end of the catheter sheath, engaging the at least one separate embolic coil with the constricted distal tip, and pushing said at least one separate embolic coil and the guidewire with its tip out from the constricted distal tip of the catheter sheath;
      (ii) withdrawing the guidewire with its tip proximally of the at least one separate embolic coil and detaching the at least one separate embolic coil from the pusher-coil assembly;
   (d) withdrawing the catheter assembly from the vessel, leaving the at least one detached separate embolic coil at the site.

* * * * *